United States Patent
Hegelund

(10) Patent No.: US 11,266,087 B1
(45) Date of Patent: Mar. 8, 2022

(54) BEET CULTIVAR NAMED AMARENA

(71) Applicant: Vilmorin-Mikado SAS, La Ménitré (FR)

(72) Inventor: Erling Hegelund, La Ménitré (FR)

(73) Assignee: Vilmorin-Mikado SAS, La Ménitré (FR)

( * ) Notice: Subject to any disclaimer, the term of this patent is extended or adjusted under 35 U.S.C. 154(b) by 0 days.

(21) Appl. No.: 17/062,216

(22) Filed: Oct. 2, 2020

(51) Int. Cl.
*A01H 6/02* (2018.01)
*A01H 5/06* (2018.01)

(52) U.S. Cl.
CPC ............... *A01H 6/024* (2018.05); *A01H 5/06* (2013.01)

(58) Field of Classification Search
None
See application file for complete search history.

(56) References Cited

U.S. PATENT DOCUMENTS 9,198,364 B2    12/2015    Becker

FOREIGN PATENT DOCUMENTS

WO    WO 2020/053313 A1    3/2020

OTHER PUBLICATIONS

Fehr ((1997) Principles of Cultivar Development vol. 1 Theory and Technique and vol. 2 Crop Species, Soybean, pp. 360-376). (Year: 1997).*

Magruder, Roy. "Descriptions of Types of Principal American Varieties of Red Garden Beets." (Year: 1940).*
Bilgen et al., "Transferring Cercospora Leaf Spot Resistance From Beta Maritima to Sugarbeet by Backcrossing," J Am Soc Sugar Beet Technol, vol. 15, No. 5, Apr. 1969, pp. 444-449.
Lewellen et al., Inheritance of Powdery Mildew Resistance in Sugar Beet Derived from *Beta vulgaris* subsp. *maritima*, Plant Disease, 85(6):627-631, Jun. 2001.
Mackay et al., The genetics of selfing with concurrent backcrossing in breeding hybrid sugar beet (*Beta vulgaris altissima* L.), Theoretical and Applied Genetics; Heidelberg vol. 98, Iss. 6-7, (May 1999): 1156-1162.
McFarlane, "Naturally Occurring Hybrids Between Sugarbeet and Beta macrocarpa in the Imperial Valley of California," Journal of the A.S.S.B.T., vol. 18, No. 3, Apr. 1975, pp. 245-251.
Sandal et al., "Backcrossing of nematode-resistant sugar beet: a second nematode resistance gene at the locus containing Hs1pro-1?," Molecular Breeding 3, 471-480 1997.
Van Geyt et al., "Natural variation within the genus *Beta* and its possible use for breeding sugar beet: A review," Euphytica 49:57-76 1990.

\* cited by examiner

*Primary Examiner* — Charles Logsdon
(74) *Attorney, Agent, or Firm* — Cooley LLP

(57) ABSTRACT

Novel beet, such as beet designated AMARENA is disclosed. In some embodiments, the disclosure relates to the seeds of beet AMARENA, to the plants and plant parts of beet AMARENA, and to methods for producing a beet plant by crossing the beet AMARENA with itself or another beet plant. Provided herewith are methods for producing a beet plant containing in its genetic material one or more transgenes and to the transgenic plants produced by that method and to methods for producing other beet plants derived from the beet AMARENA.

25 Claims, 6 Drawing Sheets

BEET CULTIVAR NAMED AMARENA

FIELD OF THE DISCLOSURE

The present disclosure relates to the field of agriculture, to a new and distinctive beet (*Beta vulgaris*) cultivar, such as cultivar designated AMARENA, and to methods of making and using such plants.

BACKGROUND OF THE DISCLOSURE

The following description includes information that may be useful in understanding the present disclosure. It is not an admission that any of the information provided herein is prior art or relevant to the presently claimed disclosures, or that any publication specifically or implicitly referenced is prior art.

Beet (*Beta vulgaris*) is a root vegetable also known as beetroot, red beet, table beet, garden beet, or more commonly as just beet. Beet is an important, valuable and popular vegetable crop used in many cuisines around the world. Beets are packed with essential vitamins, minerals and other plant compounds, some of which have medicinal properties. Thus, a continuing goal of plant breeders is to develop more stable, higher yielding beet cultivars that are agronomically sound and/or have unique properties. The reasons for this goal are to maximize the amount of yield produced on the land used to grow them as well as to improve the plant agronomic and horticultural qualities. To accomplish this goal, the beet breeder must select and develop beet plants that have the traits that result in superior cultivars.

SUMMARY OF THE DISCLOSURE

The following embodiments and aspects thereof are described in conjunction with systems, tools and methods which are meant to be exemplary, not limiting in scope.

In various embodiments, one or more of the above-described problems have been reduced or eliminated, while other embodiments are directed to other improvements. In this disclosure, 'variety' and 'cultivar' are interchangeably used.

According to the disclosure, in some embodiments, there is provided a novel beet cultivar, designated AMARENA, also interchangeably referred to as 'beet cultivar AMARENA', 'beet plant designated AMARENA', 'beet plant AMARENA', 'beet AMARENA' or 'AMARENA'. This disclosure thus relates to the seeds of beet cultivar designated AMARENA, to the plants or parts thereof of beet cultivar designated AMARENA, to plants or parts thereof consisting essentially all of the physiological and morphological characteristics of beet cultivar designated AMARENA or parts thereof, and/or having all of the physiological and morphological characteristics of beet cultivar designated AMARENA and/or having one or more or all of the characteristics of beet cultivar designated AMARENA including but not limited to as determined at the 5% significance level when grown in the same environmental conditions, and/or having one or more of the physiological and morphological characteristics of beet cultivar designated AMARENA including but not limited to as determined at the 5% significance level when grown in the same environmental conditions, and/or having all of the physiological and morphological characteristics of beet cultivar designated AMARENA including but not limited to as determined at the 5% significance level when grown in the same environmental conditions and/or having all of the physiological and morphological characteristics of beet cultivar designated AMARENA when grown in the same environmental conditions. The disclosure also relates to variants, mutants and trivial modifications of the seed or plant of beet cultivar designated AMARENA.

Plant parts of the beet cultivar AMARENA of the present disclosure are also provided, such as, but not limited to, a crown, a leaf, a flower, a cotyledon, a hypocotyl, a stem, a shoot, a root, a rootlet, a taproot, a root tip, a fruit, a stalk, a seed, an embryo, a stamen, an anther, a pistil, a pollen, an ovule, or a cell obtained from the plant cultivar. The present disclosure provides crowns, leaves, roots and taproots of the beet cultivar of the present disclosure. Such crowns, leaves, roots, taproots or parts thereof could be used as fresh products for consumption or in processes resulting in processed, canned, dried, or frozen food products comprising one or more harvested part of the beet plant AMARENA, for example harvested leaves and/or roots. The harvested part or food product can be or can comprise the beet leaves and/or roots of the beet plant AMARENA or a salad mixture comprising leaves and/or roots of the beet plant AMARENA. The food products might have undergone one or more processing steps such as, but not limited to cutting, washing, mixing, drying, freezing, squeezing, processing, canning, pickling, etc. All such products are part of the present disclosure. The present disclosure also provides plant parts or cells of beet AMARENA, wherein a plant regenerated from said plants parts or cells has one or more, or all of the phenotypic and morphological characteristics of the beet plant AMARENA, such as one or more or all of the characteristics of the beet plant AMARENA when grown in the same environmental conditions. All such products are part of the present disclosure.

The plants and seeds of the present disclosure include those that may be of an essentially derived variety as defined in section 41(3) of the Plant Variety Protection Act of The United States of America, e.g., a variety that is predominantly derived from beet cultivar designated AMARENA or from a variety that i) is predominantly derived from beet cultivar designated AMARENA, while retaining the expression of the essential characteristics that result from the genotype or combination of genotypes of beet cultivar designated AMARENA; ii) is clearly distinguishable from beet cultivar designated AMARENA; and iii) except for differences that result from the act of derivation, conforms to the initial variety in the expression of the essential characteristics that result from the genotype or combination of genotypes of the initial variety or cultivar.

In another aspect, the present disclosure provides regenerable cells. In some embodiments, the regenerable cells are for use in tissue culture of beet cultivar designated AMARENA. In some embodiments, the tissue culture is capable of regenerating plants comprising one or more or all of the physiological and morphological characteristics of beet cultivar designated AMARENA, and/or having all of the physiological and morphological characteristics of beet cultivar designated AMARENA, and/or having the physiological and morphological characteristics of beet cultivar designated AMARENA, and/or having the characteristics of beet cultivar designated AMARENA. In one embodiment, the regenerated plants have the characteristics of beet cultivar designated AMARENA including but not limited to as determined at the 5% significance level when grown in the same environmental conditions and/or have all of the physiological and morphological characteristics of beet cultivar designated AMARENA including but not limited to as determined at the 5% significance level when grown in the same environmental conditions and/or have one or more of the physiological and morphological characteristics of beet cultivar designated AMARENA including but not limited to as determined at the 5% significance level when grown in the same environmental conditions and/or have all of the physiological and morphological characteristics of beet cultivar designated AMARENA when grown in the same environmental conditions.

In some embodiments, the plant parts and cells used to produce such tissue cultures will be embryos, meristematic cells, seeds, callus, pollen, leaves, anthers, pistils, shoots, crowns, roots, rootlets, taproots, root tips, stems, petioles, heads, cotyledons, hypocotyls, ovaries, seed coat, fruits, endosperm, flowers, axillary buds or the like. Protoplasts produced from such tissue culture are also included in the present disclosure. The beet shoots, roots and whole plants regenerated from the tissue culture, as well as the heads and leaves produced by said regenerated plants are also part of the disclosure. In some embodiments, the whole plants regenerated from the tissue culture have one, more than one, or all of the physiological and morphological characteristics of beet cultivar designated AMARENA listed in Table 1, including but not limited to as determined at the 5% significance level when grown in the same environmental conditions.

The disclosure also discloses methods for vegetatively propagating a plant of the present disclosure. In the present application, vegetatively propagating can be interchangeably used with vegetative reproduction. In some embodiments, the methods comprise collecting a part of a beet cultivar designated AMARENA and regenerating a plant from said part. In some embodiments, the part can be for example a stem cutting or leaf cutting that is rooted into an appropriate medium according to techniques known by the one skilled in the art. Plants, plant parts, leaves and roots thereof produced by such methods are also included in the present disclosure. In another aspect, the plants, leaves, and roots thereof produced by such methods comprise all of the physiological and morphological characteristics of beet cultivar designated AMARENA, and/or having all of the physiological and morphological characteristics of beet cultivar designated AMARENA, and/or having the physiological and morphological characteristics of beet cultivar designated AMARENA, and/or having the characteristics of beet cultivar designated AMARENA. In some embodiments, plants and parts including leaves and roots produced by such methods consist of one, more than one, or all physiological and morphological characteristics of beet cultivar designated AMARENA when grown in the same environmental conditions.

Further included in the disclosure are methods for producing leaves, roots and/or seeds from the beet cultivar designated AMARENA. In some embodiments, the methods comprise growing a beet cultivar designated AMARENA to produce beet leaves, roots and/or seeds. In some embodiments, the methods further comprise harvesting the beet roots, leaves and/or seeds. Such beet roots, leaves and/or seeds are part of the present disclosure. In some embodiments, the beet leaves have all of the physiological and morphological characteristics of the beet roots and/or leaves of beet cultivar designated AMARENA (e.g. those listed in Table 1 and/or deposited under NCIMB No. 43761) when grown in the same environmental conditions.

Also included in this disclosure are methods for producing a beet plant. In some embodiments, the beet plant is produced by crossing the beet cultivar designated AMARENA with itself or another beet plant. In some embodiments, the other plant can be a beet AMARENA line, a been plant other than BB218 including a hybrid, or a transgenic. When crossed with itself, i.e. when AMARENA is crossed with another beet cultivar AMARENA, respectively or self-pollinated, beet cultivar AMARENA will be conserved (e.g. as an inbred). When crossed with another, different beet plant, an F1 hybrid seed is produced if the different beet plant is an inbred and a "three-way cross" seed is produced if the different beet plant is a hybrid. Such F1 hybrid seed and three-way hybrid seeds and plants produced by growing said F1 and three-way hybrid seeds are included in the present disclosure. Methods for producing an F1 and three-way hybrid beet seed comprising crossing beet cultivar AMARENA beet plant with a different beet line or hybrid, and harvesting the resultant hybrid beet seed are also part of the disclosure. The hybrid beet seeds produced by the methods comprising crossing beet cultivar AMARENA plant with a different beet plant and harvesting the resultant hybrid beet seed are included in the disclosure, as are included the hybrid beet plants or parts thereof and seeds produced by said grown hybrid beet plants.

Further included in the disclosure are methods for producing a beet seed and plants made thereof. In some embodiments, the methods comprise self-pollinating the beet cultivar AMARENA and harvesting the resultant seeds. beet seeds produced by such method are also part of the disclosure.

In another embodiment, this disclosure also relates to methods for producing other beet plants derived from beet cultivar AMARENA and to the beet plants derived by the use of methods described herein.

In some embodiments, such methods for producing a beet plant derived from the beet cultivar AMARENA comprise (a) self-pollinating the beet cultivar AMARENA plant at least once to produce a progeny plant derived from beet cultivar AMARENA; In some embodiments, the methods further comprise (b) crossing the progeny plant derived from beet cultivar AMARENA with itself or a second beet plant to produce a seed of a progeny plant of a subsequent generation; In some embodiments, the methods further comprise (c) growing the progeny plant of the subsequent generation. In some embodiments, the methods further comprise (d) crossing the progeny plant of the subsequent generation with itself or a second beet plant to produce a beet plant further derived from the beet cultivar AMARENA. In further embodiments, step (b), step (c) and/or step (d) are repeated for at least 1, 2, 3, 4, 5, 6, 7, 8, or more generations to produce a beet plant derived from the beet cultivar AMARENA. In some embodiments, within each crossing cycle, the second plant is the same plant as the second plant in the last crossing cycle. In some embodiments, within each crossing cycle, the second plant is different from the second plant in the last crossing cycle.

Another method for producing a beet plant derived from the variety AMARENA, comprises the steps of: (a) crossing the AMARENA plant with a second beet plant to produce a progeny plant derived from beet cultivar AMARENA; In some embodiments, the method further comprises (b) crossing the progeny plant derived from beet cultivar AMARENA with itself or a second beet plant to produce a seed of a progeny plant of a subsequent generation; In some embodiments, the method further comprises (c) growing the progeny plant of the subsequent generation; In some embodiments, the method further comprises (d) crossing the progeny plant of the subsequent generation with itself or a second beet plant to produce a beet plant derived from AMARENA. In a further embodiment, step (b), step (c) and/or step (d) are repeated for at least 1, 2, 3, 4, 5, 6, 7, 8, or more generations to produce a beet plant derived from AMARENA. In some embodiments, within each crossing cycle, the second plant is the same plant as the second plant in the last crossing cycle. In some embodiments, within each crossing cycle, the second plant is different from the second plant in the last crossing cycle.

In another aspect, the present disclosure provides methods of introducing a single locus conversion conferring one or more desired trait(s) into the beet AMARENA, and plants, leaves, roots and/or seeds obtained from such methods. In another aspect, the present disclosure provides methods of modifying a single locus and conferring one or more desired trait(s) into the beet AMARENA, and plants, leaves, roots and/or seeds obtained from such methods. The desired trait(s) may be, but not exclusively, a single gene. In some embodiments, the gene is a dominant allele. In some embodiments, the gene is a partially dominant allele. In some embodiments, the gene is a recessive allele. In some embodiments, the gene or genes will confer such traits, including but not limited to male sterility, herbicide resistance, insect resistance, resistance for bacterial, fungal, mycoplasma or viral disease, enhanced plant quality such as improved drought or salt tolerance, water-stress tolerance, improved standability, enhanced plant vigor, improved shelf life, delayed senescence or controlled ripening, enhanced nutritional quality such as increased sugar content or increased sweetness, increased texture, flavor and aroma, improved root length and/or size, protection for color, root shape, uniformity, length or diameter, refinement or depth, yield and recovery, improve fresh cut application, specific aromatic compounds, specific volatiles, lodging resistance, leaf/root texture, specific nutritional components. For the present disclosure and the skilled artisan, disease is understood to include, but not limited to fungal diseases, viral diseases, bacterial diseases, mycoplasma diseases, or other plant pathogenic diseases and a disease resistant plant will encompass a plant resistant to fungal, viral, bacterial, mycoplasma, and other plant pathogens. In one aspect, the gene or genes may be naturally occurring beet gene(s) and/or spontaneous or induced mutations(s). In another aspect, genes are mutated, modified, genetically engineered through the use of New Breeding Techniques described herein. In some embodiments, the method for introducing the desired trait(s) is a backcrossing process by making use of a series of backcrosses to at least one of the parent lines of beet cultivar designated AMARENA during which the desired trait(s) is maintained by selection. At least one of the parent lines of beet cultivar designated AMARENA possesses the desired trait(s) by the backcrossing process, and the desired trait(s) is inherited by the beet progeny plants by conventional breeding techniques known to breeders of ordinary skill in the art. The single gene converted plants or single locus converted plants that can be obtained by the methods are included in the present disclosure.

When dealing with a gene that has been modified, for example through New Breeding Techniques, the trait (genetic modification) could be directly modified into the newly developed beet line/cultivar of the present disclosure such as beet cultivar AMARENA. Alternatively, if the trait is not modified into each newly developed line/cultivar such as beet cultivar AMARENA, another typical method used by breeders of ordinary skill in the art to incorporate the modified gene is to take a line already carrying the modified gene and to use such line as a donor line to transfer the modified gene into the newly developed line. The same would apply for a naturally occurring trait or one arising from spontaneous or induced mutations.

In some embodiments, the backcross breeding process of beet cultivar AMARENA comprises (a) crossing beet cultivar AMARENA with plants that comprise the desired trait(s) to produce F1 progeny plants. In some embodiments, the process further comprises (b) selecting the F1 progeny plants that have the desired trait(s); In some embodiments, the process further comprises (c) crossing the selected F1 progeny plants with the beet cultivar AMARENA plants to produce backcross progeny plants; In some embodiments, the process further comprises (d) selecting for backcross progeny plants that have the desired trait(s) and essentially all of the physiological and morphological characteristics of the beet cultivar AMARENA to produce selected backcross progeny plants; In some embodiments, the process further comprises (e) repeating steps (c) and (d) one, two, three, four, five six, seven, eight, nine or more times in succession to produce selected, second, third, fourth, fifth, sixth, seventh, eighth, ninth or higher backcross progeny plants that have the desired trait(s) and comprise essentially of all of the physiological and morphological characteristics of the beet cultivar AMARENA, and/or have the desired trait(s) and essentially all of the physiological and morphological characteristics of the beet cultivar AMARENA, and/or have all of the desired trait(s) and essentially all of the physiological and morphological characteristics of the beet cultivar AMARENA, including but not limited to when grown in the same environmental conditions or including but not limited to at a 5% significance level when grown in the same environmental conditions. The beet plants or seed produced by the methods are also part of the disclosure. Backcrossing breeding methods, well known to one skilled in the art of plant breeding will be further developed in subsequent parts of the specification.

In an embodiment of this disclosure is a method of making a backcross conversion of beet cultivar AMARENA. In some embodiments, the method comprises crossing beet cultivar AMARENA with a donor plant comprising a mutant gene(s), a naturally occurring gene(s) or a gene(s) and/or sequences modified through New Breeding Techniques conferring one or more desired traits to produce F1 progeny plants. In some embodiments, the method further comprises selecting an F1 progeny plant comprising the naturally occurring gene(s) mutant gene(s) or modified gene(s) and/or sequences midwifed through New Breeding Techniques conferring the one or more desired traits. In some embodiments, the method further comprises backcrossing the selected progeny plant to the beet cultivar AMARENA. This method may further comprise the step of obtaining a molecular marker profile of the beet cultivar AMARENA and using the molecular marker profile to select for the progeny plant with the desired trait and the molecular marker profile of the beet cultivar AMARENA. The plants or parts thereof produced by such methods are also part of the present disclosure.

In some embodiments of the disclosure, the number of loci that may be transferred and/or backcrossed into the beet cultivar AMARENA is at least 1, 2, 3, 4, 5 or more. A single locus may contain several genes. A single locus conversion also allows for making one or more site specific changes to the plant genome, such as, without limitation, one or more nucleotide change, deletions, insertions, substitutions etc. In some embodiments, the single locus conversion is performed by genome editing, a.k.a. genome editing with engineered nucleases (GEEN). In some embodiments, the genome editing comprises using one or more engineered nucleases. In some embodiments, the engineered nucleases include, but are not limited to Zinc finger nucleases (ZFNs), Transcription Activator-Like Effector Nucleases (TALENs), the CRISPR/Cas system, engineered meganuclease, re-engineered homing endonucleases, and endonucleases for DNA guided genome editing (Gao et al., Nature Biotechnology (2016), doi: 10.1038/nbt.3547). In some embodiments, the single locus conversion changes one or several nucleotides of the plant genome. Such genome editing techniques are some of the techniques now known by the person skilled in the art and herein are collectively referred to as "New Breeding Techniques". In some embodiments, one or more above-mentioned genome editing method is directly applied on a plant of the present disclosure, Accordingly, a cell containing edited genome, or a plant part containing such cell can be isolated and used to regenerate a novel plant which has a new trait conferred by said genome editing, and essentially all of the physiological and morphological characteristics of beet cultivar AMARENA.

The disclosure further provides methods for developing beet plants in a beet plant breeding program using plant breeding techniques including but not limited to, recurrent selection, backcrossing, pedigree breeding, genomic selection, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites, Single Nucleotide Polymorphism (SNP), etc.) enhanced selection, genetic marker enhanced selection and transformation. Seeds, beet plants, and parts thereof produced by such breeding methods are also part of the disclosure.

The disclosure also relates to variants, mutants and trivial modifications of the seed or plant of the beet cultivar AMARENA. Variants, mutants and trivial modifications of the seed or plant of beet cultivar AMARENA can be generated by methods available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knockouts/knock-ins, antisense oligonucleotides, and RNA interference and other techniques such as the New Breeding Techniques. For more information of mutagenesis in plants, such as agents, protocols, see Acquaah et al. (Principles of plant genetics and breeding, Wiley-Blackwell, 2007, ISBN 1405136464, 9781405136464, which is herein incorporated by reference in its entity).

The disclosure also relates to a mutagenized population of the beet cultivar AMARENA and methods of using such populations. In some embodiments, the mutagenized population can be used in screening for new beet plants which comprise essentially one or more or all of the morphological and physiological characteristics of beet cultivar AMARENA. In some embodiments, the new beet plants obtained from the screening process comprise essentially all of the morphological and physiological characteristics of the beet cultivar AMARENA, and one or more additional or different morphological and physiological characteristics that beet cultivar AMARENA does not have.

This disclosure is also directed to methods for producing a beet plant by crossing a first parent beet plant with a second parent beet plant wherein either the first or second parent beet plant is a beet cultivar AMARENA. Further, both first and second parent beet plants can come from the beet cultivar AMARENA. Further, the beet cultivar AMARENA can be self-pollinated i.e. the pollen of a beet cultivar AMARENA can pollinate the ovule of the same beet cultivar AMARENA, respectively. When crossed with another beet plant, a hybrid seed is produced. Such methods of hybridization and self-pollination are well known to those skilled in the art of breeding.

A beet cultivar such as beet cultivar AMARENA has been produced through several cycles of self-pollination and is therefore to be considered as a homozygous plant or line. An inbred line can also be produced though the dihaploid system which involves doubling the chromosomes from a haploid plant or embryo thus resulting in an inbred line that is genetically stable (homozygous) and can be reproduced without altering the inbred line: Haploid plants could be obtained from haploid embryos that might be produced from microspores, pollen, anther cultures or ovary cultures or spontaneous haploidy. The haploid embryos may then be doubled by chemical treatments such as by colchicine or be doubled autonomously. The haploid embryos may also be grown into haploid plants and treated to induce the chromosome doubling. In either case, fertile homozygous plants are obtained. A hybrid variety is classically created through the fertilization of an ovule from an inbred parental line by the pollen of another, different inbred parental line. Due to the homozygous state of the inbred line, the produced gametes carry a copy of each parental chromosome. As both the ovule and the pollen bring a copy of the arrangement and organization of the genes present in the parental lines, the genome of each parental line is present in the resulting F1 hybrid, theoretically in the arrangement and organization created by the plant breeder in the original parental line.

As long as the homozygosity of the parental lines is maintained, the resulting hybrid cross shall be stable. The F1 hybrid is then a combination of phenotypic characteristics issued from two arrangement and organization of genes, both created by a person skilled in the art through the breeding process.

Still further, this disclosure is also directed to methods for producing a beet cultivar AMARENA-derived beet plant by crossing beet cultivar AMARENA with a second beet plant. In some embodiments, the methods further comprise obtaining a progeny seed from the cross. In some embodiments, the methods further comprise growing the progeny seed, and possibly repeating the crossing and growing steps with the beet cultivar AMARENA-derived plant from 0 to 7, or more times. Thus, any such methods using the beet cultivar AMARENA are part of this disclosure: selfing, backcrosses, hybrid production, crosses to populations, and the like. All plants produced using beet cultivar AMARENA as a parent are within the scope of this disclosure, including plants derived from beet cultivar AMARENA. In some embodiments, such plants have one, more than one, or all of the physiological and morphological characteristics of beet cultivar designated AMARENA when grown in the same environmental conditions. In some embodiments, such plants might exhibit additional and desired characteristics or traits such as high seed yield, high seed germination, seedling vigor, early maturity, high yield, disease tolerance or resistance, lodging resistance, and adaptability for soil and climate conditions. Consumer-driven traits, such as a preference for a given size, shape, color, texture, taste, firmness, sugar content of leaf and/or root are other traits that may be incorporated into new beet plants developed by this disclosure.

A beet plant can also be propagated vegetatively. A part of the plant, for example a root, a shoot or a leaf tissue, is collected, and a new plant is obtained from the part. Such part typically comprises an apical meristem of the plant. The collected part is transferred to a medium allowing development of a plantlet, including for example rooting or development of shoots, or is grafted onto soil and/or ground. This is achieved using methods well-known in the art. Accordingly, in one embodiment, a method of vegetatively propagating a plant of the present disclosure comprises collecting a part of a plant according to the present disclosure, e.g. a shoot tissue, and obtaining a plantlet from said part. In one embodiment, a method of vegetatively propagating a plant of the present disclosure comprises: (a) collecting tissue of a plant of the present disclosure; (b) rooting said proliferated shoots to obtain rooted plantlets. In one embodiment, a method of vegetatively propagating a plant of the present disclosure comprises: (a) collecting tissue of a plant of the present disclosure; (b) cultivating said tissue to obtain proliferated shoots; (c) rooting said proliferated shoots to obtain rooted plantlets. In one embodiment, such method further comprises growing a plant from said plantlets. In one embodiment, a root and/or a leaf is harvested from said plant. In one embodiment, a leaf is harvested from said plant. In one embodiments, such plants, roots and leaves have all of the physiological and morphological characteristics of plants, roots and leaves of beet cultivar AMARENA when grown in the same environmental conditions. In one embodiment, the roots and/or leaves is processed into products prepared such as fresh, pickled, squeezed, processed, canned, dried, and/or frozen food product.

In some embodiments, the food products prepared using beet cultivar AMARENA, and plant parts thereof, can be provided in any useful form, including but not limited to being fresh, pickled, dried, canned and/or frozen. The food products may be in any of the different forms suitable for such food products, including but not limited to being whole, sliced, diced, pureed and/or juiced. Exemplary food products include, but are not limited to fresh salad mixes, spring mix, beets tops, pickled products, canned products, frozen products, dried chips, squeezed juice, dried juice powder, as a food dye, as an additive, and as a puree, which can be used in drink blends.

In some embodiments, the present disclosure teaches a seed of beet cultivar AMARENA, wherein a representative sample of seed of said beet cultivar is deposited under NCIMB No. 43761.

In some embodiments, the present disclosure teaches a beet plant, or a part thereof, produced by growing the deposited AMARENA seed.

In some embodiments, the present disclosure teaches beet plant parts, wherein the beet part is selected from the group consisting of: a crown, a leaf, a flower, a cotyledon, a hypocotyl, a stem, a shoot, a root, a rootlet, a taproot, a root tip, a fruit, a stalk, a seed, an embryo, a stamen, an anther, a pistil, a pollen, an ovule, and a cell. In some embodiments, a beet leaf and/or root is produced from the plant described herewith.

In some embodiments, the present disclosure teaches a beet plant, or a part thereof, having all of the characteristics of beet cultivar AMARENA deposited under NCIMB No. 43761 including but not limited to when grown in the same environmental conditions.

In some embodiments, the present disclosure teaches a beet plant, or a part thereof, having all of the physiological and morphological characteristics of beet cultivar AMARENA, wherein a representative sample of seed of said beet plant was deposited under NCIMB No. 43761. In some embodiments, the present disclosure teaches the plant or a plant regenerated from the plant part or the plant cell has all of the physiological and morphological characteristics of the deposited beet when grown under the same environmental conditions.

In some embodiments, the present disclosure teaches a tissue culture of regenerable cells produced from the plant or plant part grown from the deposited beet cultivar AMARENA seed, wherein cells of the tissue culture are produced from a plant part selected from the group consisting of protoplasts, embryos, meristematic cells, seeds, callus, pollen, leaves, anthers, pistils, shoots, crowns, roots, rootlets, taproots, root tips, anthers, stems, petioles, fruits, axillary buds, cotyledons and hypocotyls. In some embodiments, the plant part includes protoplasts produced from a plant grown from the deposited beet cultivar AMARENA seed.

In some embodiments, the present disclosure teaches a composition comprising regenerable cells produced from the plant or plant part grown from the deposited beet cultivar AMARENA seed, or other plant part or plant cell. In some embodiments, the composition comprises a growth media. In some embodiments, the growth media is solid or a synthetic cultivation medium.

In some embodiments, the composition is a beet plant regenerated from the tissue culture from a plant grown from the deposited beet cultivar AMARENA seed, said plant having the characteristics of beet cultivar AMARENA deposited under NCIMB No. 43761.

In some embodiments, the present disclosure teaches a beet leaf and/or root produced from plants grown from the deposited beet cultivar AMARENA seed. In some embodiments, such roots and/or leaves have all of the physiological and morphological characteristics of beet AMARENA roots and/or leaves when grown in the same environmental conditions.

In some embodiments, the methods of producing a beet leaf and/or root comprise (a) growing the beet plant from deposited beet cultivar AMARENA seed to produce a beet leaf and/or root, and (b) harvesting said beet leaf and/or root. In some embodiments, the present disclosure also teaches a beet leaf and/or root produced by the method of producing beet root as described above. In one embodiments, such roots and/or leaves have all of the physiological and morphological characteristics of roots and/or leaves of beet cultivar AMARENA (e.g. those listed in Table 1 and/or deposited under NCIMB No. 43761) when grown in the same environmental conditions.

In some embodiments, the present disclosure teaches methods for producing a beet seed comprising crossing a first parent beet plant with a second parent beet plant and harvesting the resultant beet seed, wherein said first parent beet plant and/or second parent beet plant is the beet plant produced from the deposited beet cultivar AMARENA seed. In some embodiments, a beet seed is produced by the methods of producing the beet seed as described above. In one embodiments, such seeds have all of the characteristics of the deposited beet cultivar AMARENA including but not limited to when grown in the same environmental conditions.

In some embodiments, the present disclosure teaches methods for producing a beet seed comprising self-pollinating the beet plant grown from the deposited beet cultivar AMARENA seed and harvesting the resultant beet seed.

In some embodiments, the present disclosure teaches the seed produced by any of the above described methods.

In some embodiments, the present disclosure teaches methods of vegetatively propagating the beet plant grown from the deposited beet cultivar AMARENA seed, said method comprising (a) collecting a part of a plant grown from the deposited beet cultivar AMARENA seed and (b) regenerating a plant from said part.

In some embodiments, the method further comprises harvesting a beet leaf and/or root from said vegetatively propagated plant.

In some embodiments, the present disclosure teaches the plant, the roots and leaves thereof of plants vegetatively propagated from plant parts of plants grown from the deposited beet cultivar AMARENA seed. In one embodiments, such plant, roots and/or leaves have all of the physiological and morphological characteristics of the deposited beet cultivar AMARENA plant, roots and/or leaves thereof (e.g. those listed in Table 1) when grown in the same environmental conditions.

In some embodiments, the present disclosure teaches methods of producing a beet plant derived from the beet cultivar AMARENA. In some embodiment the methods comprise (a) self-pollinating the plant grown from the deposited beet cultivar AMARENA seed at least once to produce a progeny plant derived from beet cultivar AMARENA. In some embodiments, the method further comprises (b) crossing the progeny plant derived from beet cultivar AMARENA with itself or a second beet plant to produce a seed of a progeny plant of a subsequent generation and; (c) growing the progeny plant of the subsequent generation from the seed, and crossing the progeny plant of the subsequent generation with itself or a second beet plant to produce a beet plant derived from the beet cultivar AMARENA. In some embodiments said methods further comprise the step of: (d) repeating steps (b) and/or (c) for at least 1, 2, 3, 4, 5, 6, 7 or more generation to produce a beet plant derived from the beet cultivar AMARENA.

In some embodiments, the present disclosure teaches methods of producing a beet plant derived from the beet cultivar AMARENA, the methods comprising (a) crossing the plant grown from the deposited beet cultivar AMARENA seed with a second beet plant to produce a progeny plant derived from the beet cultivar AMARENA. In some embodiments, the method further comprises (b) crossing the progeny plant derived from the beet cultivar AMARENA with itself or a second beet plant to produce a seed of a progeny plant of a subsequent generation and; (c) growing the progeny plant of the subsequent generation from the seed; (d) crossing the progeny plant of the subsequent generation with itself or a second beet plant to produce a beet plant derived from the beet cultivar AMARENA. In some embodiments said methods further comprise the step of: (e) repeating step (b), (c) and/or (d) for at least 1, 2, 3, 4, 5, 6, 7 or more generation to produce a beet plant derived from the beet cultivar AMARENA.

In some embodiments, the present disclosure teaches plants grown from the deposited beet cultivar AMARENA seed wherein said plants comprise a single locus conversion. As used herein, the term "a" or "an" refers to one or more of that entity; for example, "a single locus conversion" refers to one or more single locus conversions or at least one single locus conversion. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

In some embodiments, the present disclosure teaches a method of producing a plant of beet cultivar designated AMARENA comprising at least one desired trait, the method comprising introducing a single locus conversion conferring the desired trait into beet cultivar designated AMARENA, whereby a plant of beet cultivar designated AMARENA comprising the desired trait is produced.

In some embodiments, the present disclosure teaches a beet plant, comprising a single locus conversion and essentially all of the characteristics of beet cultivar designated AMARENA when grown under the same environmental conditions, wherein a representative sample of seed of said hybrid has been deposited under NCIMB No. 43761. In other embodiments, the single locus conversion is introduced into the plant by the use of recurrent selection, mutation breeding, wherein said mutation breeding selects for a mutation that is spontaneous or artificially induced, backcrossing, pedigree breeding, haploid/double haploid production, marker-assisted selection, genetic transformation, genomic selection, Zinc finger nuclease (ZFN) technology, oligonucleotide directed mutagenesis, cisgenesis, intragenesis, RNA-dependent DNA methylation, agro-infiltration, Transcription Activation-Like Effector Nuclease (TALENs), CRISPR/Cas system, engineered meganuclease, re-engineered homing endonuclease, and DNA guided genome editing.

In some embodiments, the plant comprises 1, 2, 3, 4, 5, 6, 7, 8, 9, 10, or more single locus conversions. In some embodiments, the plant comprises no more than 1, 2, 3, 4, 5, 6, 7, 8, 9, or 10 single locus conversions, but essentially all of the other physiological and morphological characteristics of the deposited beet cultivar plant AMARENA. In some embodiments, the plant comprises at least one single locus conversion and essentially all of the physiological and morphological characteristics of the deposited beet cultivar plant AMARENA. In other embodiments, the plant comprises one single locus conversion and essentially all of the other physiological and morphological characteristics of the deposited beet cultivar plant AMARENA.

In some embodiments, said single locus conversion confers said plants with a trait selected from the group consisting of male sterility, male fertility, herbicide resistance, insect resistance, resistance for bacterial, fungal, mycoplasma or viral disease, enhanced plant quality such as improved drought or salt tolerance, water stress tolerance, improved standability, enhanced plant vigor, improved shelf life, delayed senescence or controlled ripening, increased nutritional quality such as increased sugar content or increased sweetness, increased texture, flavor and aroma, improved fruit length and/or size, protection for color, fruit shape, uniformity, length or diameter, refinement or depth lodging resistance, yield and recovery when compared to a suitable check/comparison plant. In further embodiments, the single locus conversion confers said plant with herbicide resistance.

In some embodiments, the check plant is a beet cultivar AMARENA not having said single locus conversion conferring the desired trait(s). In some embodiments, the at least one single locus conversion is an artificially mutated gene or a gene or nucleotide sequence modified through the use of New Breeding Techniques.

In some embodiments, the present disclosure teaches methods for producing nucleic acids, comprising isolating nucleic acids from the plant grown from the deposited AMARENA seed, or a part, or a cell thereof. In some embodiments, the present disclosure teaches methods for producing a second beet plant, comprising applying plant breeding techniques to the plant grown from the deposited AMARENA seed, or part thereof to produce the second beet plant.

In some embodiments, the present disclosure teaches methods of introducing a desired trait into a beet plant designated AMARENA, the method comprising: (a) crossing a beet AMARENA plant grown from beet AMARENA seed, wherein a representative sample of seed has been deposited under NCIMB No. 43761, with another beet plant or a *Beta* plant sexually compatible with beet that comprises a desired trait to produce F1 progeny plants; (b) selecting one or more progeny plants that have the desired trait to produce selected progeny plants; (c) crossing the selected progeny plants with the beet AMARENA plants to produce backcross progeny plants; (d) selecting for backcross progeny plants that have the desired trait and essentially all of the physiological and morphological characteristics of the deposited beet AMARENA to produce selected backcross progeny plants; and (e) repeating steps (c) and (d) three or more times in succession to produce selected fourth or higher backcross progeny plants that comprise the desired trait and essentially all of the physiological and morphological characteristics of the deposited beet AMARENA. In further embodiments, methods of introducing a desired trait into a beet plant designated AMARENA, the method comprising: crossing a beet AMARENA plant grown from beet AMARENA seed, wherein a representative sample of seed has been deposited under NCIMB No. 43761, with another species not in the genus *Beta* for intergeneric crosses if the cross is compatible.

In some embodiments, the present disclosure provides a method of producing a commodity plant product comprising collecting the commodity plant product from the plant of the present disclosure. The commodity plant product produced by said method is also part of the present disclosure.

In addition to the exemplary aspects and embodiments described above, further aspects and embodiments will become apparent by study of the following descriptions.

DETAILED DESCRIPTION OF THE DISCLOSURE

Definitions

Figure 1:
FIG. 1 shows AMARENA tops and roots after washing.
Figure 2:
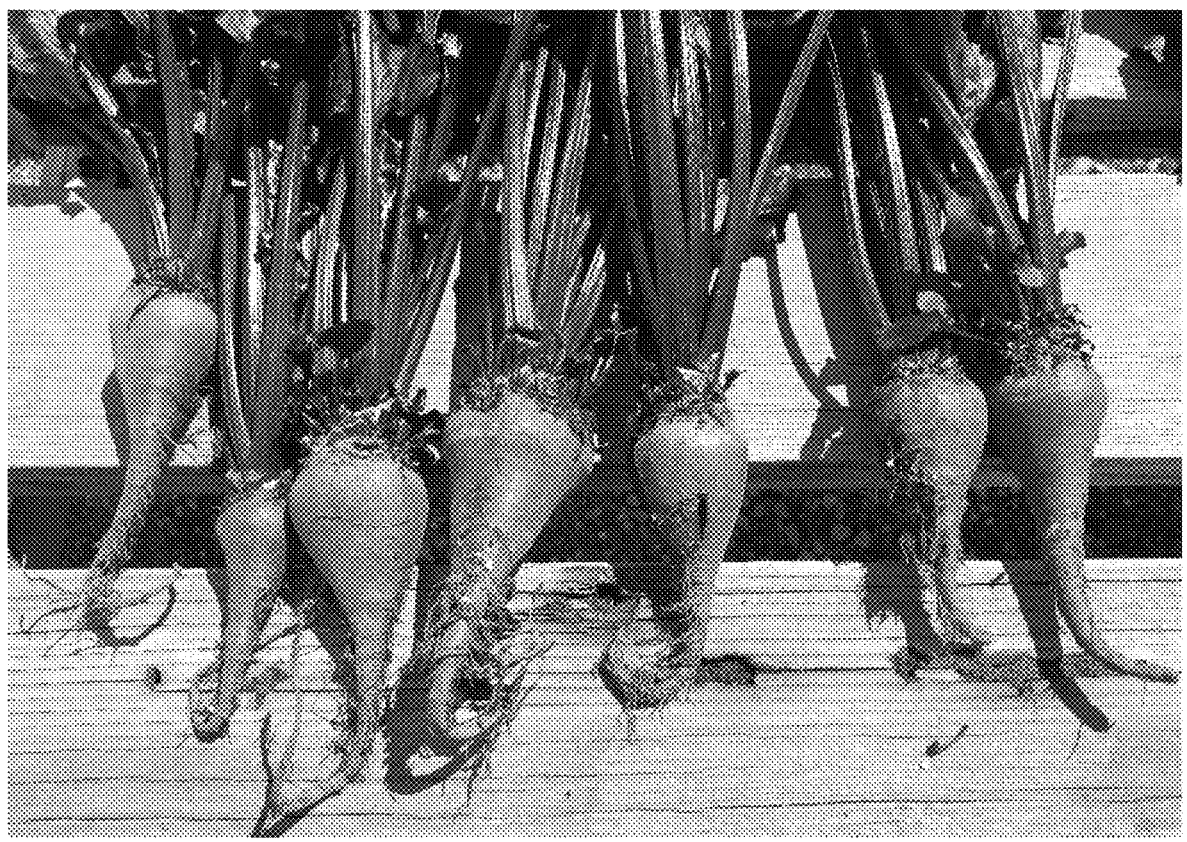
FIG. 2 shows AMARENA tops and roots before washing.
Figure 3:
FIG. 3 shows longitudinal section of AMARENA roots.
Figure 4:
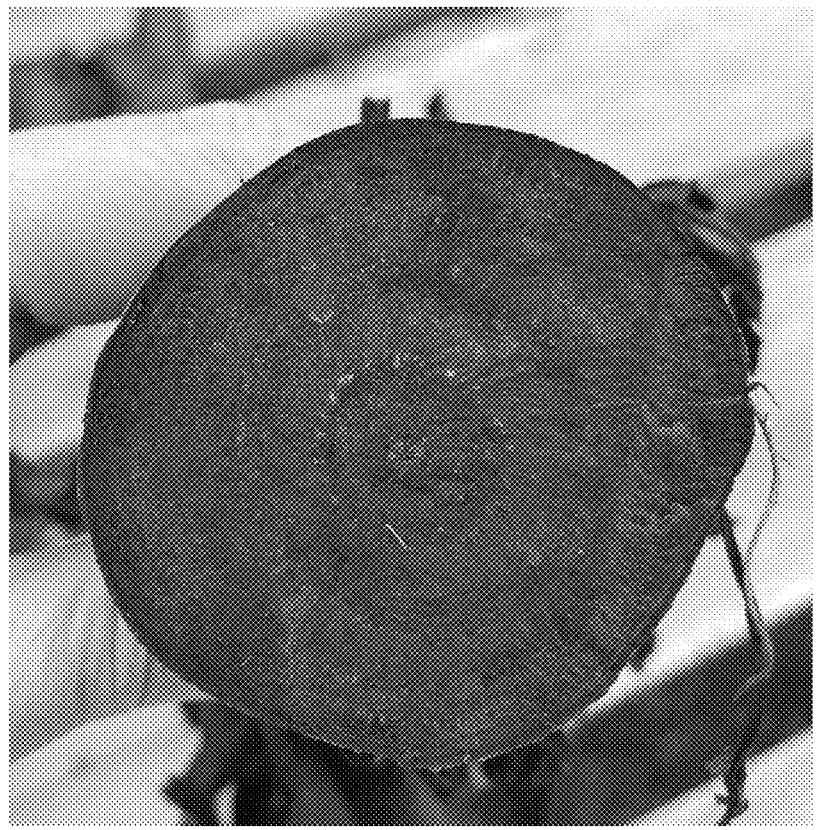
FIG. 4 shows cross section of AMARENA roots.
Figure 5:
FIG. 5 shows 7 days old AMARENA seedlings with cotyledons (left side) and hypocotyls (right side).
Figure 6:
FIG. 6 shows a mature leaf (with blade and petiole) of 55 days old AMARENA plant.

In the description and tables that follow, a number of terms are used. In order to provide a clear and consistent understanding of the specification and claims, including the scope to be given such terms, the following definitions are provided:

Adaptability. A plant that has adaptability is a plant able to grow well in different growing conditions (climate, soils, etc.).

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bolting. Bolting refers to the transition from the vegetative stage to the reproductive stage. Bolting (i.e., stem elongation) is the initial and clearly visible transition from vegetative growth where a plant continues to produce new leaves to reproductive growth where a plant produces an inflorescence. Bolting is the development of a flowering stalk typical of a biennial plant's life cycle, before a plant produces a seed crop. Bolting is typically caused by late planting when temperatures are low enough to cause vernalization of the plants.

Commodity plant product. A "commodity plant product" refers to any composition or product that is comprised of material derived from a plant, seed, plant cell, or plant part of the present disclosure. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, paper, tea, coffee, silage, crushed of whole grain, and any other food for human or animal consumption; and biomass and fuel products; and raw material in industry.

Collection of seeds. In the context of the present disclosure a collection of seeds is a grouping of seeds mainly containing similar kind of seeds, for example hybrid seeds having the inbred line of the disclosure as a parental line, but that may also contain, mixed together with this first kind of seeds, a second, different kind of seeds, of one of the inbred parent lines, for example the inbred line of the present disclosure. A commercial bag of hybrid seeds having the inbred line of the disclosure as a parental line and containing also the inbred line seeds of the disclosure would be, for example such a collection of seeds.

Decreased vigor. A plant having a decreased vigor in the present disclosure is a plant that, compared to other plants has a less vigorous appearance for vegetative and/or reproductive characteristics including shorter plant height, small root size, fewer leaves or other characteristics. In some embodiments, a plant has a decreased vigor due to inbreeding depression.

Earliness. The earliness relates the number of days from seeding to harvest.

Essentially all of the physiological and morphological characteristics. A plant having essentially all of the physiological and morphological characteristics means a plant having all of the physiological and morphological characteristics of a plant of the present disclosure, except, for example, additional traits and/or mutations which do not materially affect the plant of the present disclosure, or, a desired characteristic(s), which can be indirectly obtained from another plant possessing at least one single locus conversion via a conventional breeding program (such as backcross breeding) or directly obtained by introduction of at least one single locus conversion via New Breeding Techniques. In some embodiments, one of the non-limiting examples for a plant having (and/or comprising) essentially all of the physiological and morphological characteristics shall be a plant having all of the physiological and morphological characteristics of a plant of the present disclosure other than desired, additional trait(s)/characteristic(s) conferred by a single locus conversion including, but not limited to, a converted or modified gene.

Immunity to disease(s) and or insect(s). A beet plant which is not subject to attack or infection by specific disease(s) and or insect(s) is considered immune.

Intermediate resistance to disease(s) and or insect(s). A beet plant that restricts the growth and development of specific disease(s) and or insect(s), but may exhibit a greater range of symptoms or damage compared to resistant plants. Intermediate resistant plants will usually show less severe symptoms or damage than susceptible plant varieties when grown under similar environmental conditions and/or specific disease(s) and or insect(s) pressure, but may have heavy damage under heavy pressure. Intermediate resistant beet plants are not immune to the disease(s) and or insect(s).

Maturity (Date). Maturity refers to the stage when plants are of full size or optimum weight, and in marketable form or shape to be of commercial or economic value.

New Breeding Techniques: New breeding techniques (NBTs) are said of various new technologies developed and/or used to create new characteristics in plants through genetic variation, the aim being targeted mutagenesis, targeted introduction of new genes or gene silencing (RdDM). The following breeding techniques are within the scope of NBTs: targeted sequence changes facilitated through the use of Zinc finger nuclease (ZFN) technology (ZFN-1, ZFN-2 and ZFN-3, see U.S. Pat. No. 9,145,565, incorporated by reference in its entirety), Oligonucleotide directed mutagenesis (ODM, a.k.a., site-directed mutagenesis), Cisgenesis and intragenesis, epigenetic approaches such as RNA-dependent DNA methylation (RdDM, which does not necessarily change nucleotide sequence but can change the biological activity of the sequence), Grafting (on GM rootstock), Reverse breeding, Agro-infiltration for transient gene expression (agro-infiltration "sensu stricto", agro-inoculation, floral dip), Transcription Activator-Like Effector Nucleases (TALENs, see U.S. Pat. Nos. 8,586,363 and 9,181,535, incorporated by reference in their entireties), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), engineered meganuclease, re-engineered homing endonucleases, DNA guided genome editing (Gao et al., Nature Biotechnology (2016), doi: 10.1038/nbt.3547, incorporated by reference in its entirety), and Synthetic genomics. A major part of today's targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques—State-of-the-art and prospects for commercial development", which is incorporated by reference in its entirety.

Plant adaptability. A plant having good plant adaptability means a plant that will perform well in different growing conditions and seasons.

Plant cell. As used herein, the term "plant cell" includes plant cells whether isolated, in tissue culture or incorporated in a plant or plant part.

Plant Part. As used herein, the term "plant part", "part thereof" or "parts thereof" includes plant cells, plant protoplasts, plant cell tissue cultures from which beet plants can be regenerated, plant calli, plant clumps and plant cells that are intact in plants or parts of plants, such as embryos, pollen, ovules, flowers, seeds, stems, crowns, roots, rootlets, taproots, anthers, pistils, root tips, leaves, meristematic cells, axillary buds, hypocotyls cotyledons, ovaries, seed coat endosperm and the like. In some embodiments, the plant part at least comprises at least one cell of said plant. In some embodiments, the plant part is further defined as a pollen, a meristem, a cell or an ovule. In some embodiments, a plant regenerated from the plant part has all of the phenotypic and morphological characteristics of a beet of the present disclosure, including but not limited to as determined at the 5% significance level when grown in the same environmental conditions.

Quantitative Trait Loci (QTL). Quantitative trait loci refer to genetic loci that control to some degree numerically representable traits that are usually continuously distributed.

Regeneration. Regeneration refers to the development of a plant from tissue culture.

Resistance to disease(s) and or insect(s). A beet plant that restricts highly the growth and development of specific disease(s) and or insect(s) under normal disease(s) and or insect(s) attack pressure when compared to susceptible plants. These beet plants can exhibit some symptoms or damage under heavy disease(s) and or insect(s) pressure. Resistant beet plants are not immune to the disease(s) and or insect(s).

RHS. RHS refers to the Royal Horticultural Society of England which publishes an official botanical color chart quantitatively identifying colors according to a defined numbering system. The chart may be purchased from Royal Hort. Society Enterprise Ltd. RHS Garden; Wisley, Woking, Surrey GU236QB, UK.

Single locus converted (conversion). Single locus converted (conversion) plants refer to plants which are developed by a plant breeding technique called backcrossing, wherein essentially all of the desired morphological and physiological characteristics of a plant are recovered in addition to a single locus transferred into the plant via the backcrossing technique or via genetic engineering. A single locus converted plant can also be referred to a plant with a single locus conversion obtained though simultaneous and/ or artificially induced mutagenesis or through the use of New Breeding Techniques described in the present disclosure. In some embodiments, the single locus converted plant has essentially all of the desired morphological and physiological characteristics of the original variety in addition to a single locus converted by spontaneous and/or artificially induced mutations, which is introduced and/or transferred into the plant by the plant breeding techniques such as backcrossing. In other embodiments, the single locus converted plant has essentially all of the desired morphological and physiological characteristics of the original variety in addition to a single locus, gene or nucleotide sequence(s) converted, mutated, modified or engineered through the New Breeding Techniques taught herein. In the present disclosure, single locus converted (conversion) can be interchangeably referred to single gene converted (conversion).

Susceptible to disease(s) and or insect(s). A beet plant that is susceptible to disease(s) and or insect(s) is defined as a beet plant that has the inability to restrict the growth and development of specific disease(s) and or insect(s). Plants that are susceptible will show damage when infected and are more likely to have heavy damage under moderate levels of specific disease(s) and or insect(s).

Tolerance to abiotic stresses. A beet plant that is tolerant to abiotic stresses has the ability to endure abiotic stress without serious consequences for growth, appearance and yield.

Uniformity. Uniformity, as used herein, describes the similarity between plants or plant characteristics which can be a described by qualitative or quantitative measurements.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants).

Yield. The yield refers to the actual yield of the beet at harvest.

Beet Plants

Beet, *Beta vulgaris* is a plant which is included in the subfamily Betoideae of the family Amaranthaceae. It is the economically most important crop of the large order Caryophyllales. It has several cultivar groups: the sugar beet, of greatest importance to produce table sugar; the root vegetable known as the beetroot or garden beet; the leaf vegetable known as chard or spinach beet; and mangelwurzel, which is a fodder crop. Three subspecies are typically recognized, but all cultivated beets fall into the subspecies *Beta vulgaris* subsp. *vulgaris*. The wild ancestor of the cultivated beets is the sea beet (*Beta vulgaris* subsp. *maritima*), and its Center of Origin lies in the Mediterranean region.

The beetroot is the taproot portion of a beet plant, usually known in Canada and the USA as beets, while the vegetable is referred to as beetroot in British English. It is also known as the table beet, garden beet, red beet, dinner beet or golden beet. It is one of several cultivar groups of *Beta vulgaris* grown for their edible taproots and leaves (called beet greens). These have been classified as *B. vulgaris* subsp. *vulgaris* 'Conditiva' Group.

*Beta vulgaris* (beet) is an herbaceous biennial or, rarely, perennial plant. Cultivated forms of beets are mostly biennial. The plant is usually erected with a long main root and a rosette of leaves growing on stems. The roots of cultivated forms are dark red, white, or yellow and moderately to strongly swollen and fleshy (subsp. *vulgaris*); or brown, fibrous, sometimes swollen and woody in the wild subspecies. The stems grow erect or, in the wild forms, often procumbent; they are simple or branched in the upper part and their surface is ribbed and striate. The basal leaves have a long petiole (which may be thickened and red, white, or yellow in some cultivars). The simple leaf blade is oblanceolate to heart-shaped, dark green to dark red, slightly fleshy, usually with a prominent midrib, with entire or undulate margin, 5-20 cm long on wild plants (often much larger in cultivated plants about 20-40cm). The upper leaves are smaller, their blades are rhombic to narrowly lanceolate. (Shultz, L. M 2003 *Beta vulgaris*. In: Flora of North America Editorial Committee (eds.): Flora of North America North of Mexico, Volume 4: "Magnoliophyta: Caryophyllidae", part 1., Oxford University Press, New York, p. 266-267; Zhu G et al 2003 *Beta vulgaris* In: Zhengyi, W., Raven, P. H., & Hong, D. (eds.): Flora of China. Volume 5: Ulmaceae through Basellaceae. Science Press/Missouri Botanical Garden Press, Beijing/St. Louis, p. 354.)

The plant produces sessile green flowers and can reach 1-2 m in height. Beets are usually grown as annual plants and harvested after one growing season. The flowers are produced in dense spike-like, basally interrupted inflorescences. Very small flowers sit in one- to three- (rarely eight-) flowered glomerules in the axils of short bracts or in the upper half of the inflorescence without bracts. The hermaphrodite flowers are urn-shaped, green or tinged reddish, and consist of five basally connate perianth segments (tepals), five stamens, and a semi-inferior ovary with two-three stigmas. The perianths of neighboring flowers are often fused. Flowers are wind-pollinated or insect-pollinated, the former method being more important. (Flores Olvera H. et al. 2008 "Floral and Inflorescence Morphology and Ontogeny in *Beta vulgaris*, with Special Emphasis on the Ovary Position". Annals of Botany. 102 (4): 643-651; Free, J. B. et al. 1975 "Insect pollination of sugar-beet (*Beta vulgaris*) seed crops". Annals of Applied Biology. 81 (2): 127-134).

In fruit, the glomerules of flowers form connate hard clusters. The fruit (utricle) is enclosed by the leathery and incurved perianth, and is immersed in the swollen, hardened perianth base. The horizontal seed is lenticular, 2-3 mm, with a red-brown, shiny seed coat. The seed contains an annular embryo and copious perisperm (feeding tissue). (Shultz, L. M 2003 *Beta vulgaris*. In: Flora of North America Editorial Committee (eds.): Flora of North America North of Mexico, Volume 4: "Magnoliophyta: Caryophyllidae", part 1., Oxford University Press, New York, p. 266-267; Zhu G et al 2003 *Beta vulgaris* In: Zhengyi, W., Raven, P. H., & Hong, D. (eds.): Flora of China. Volume 5: Ulmaceae through Basellaceae. Science Press/Missouri Botanical Garden Press, Beijing/St. Louis, p. 354.)

There are 18 chromosomes found in 2 sets, which makes beets diploid (2n=18).

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm.

In beet, these important traits may include higher yield of roots or leaves, improved leaf color, consistent leaf color at the juvenile stage in warm as well as cool conditions, agronomic quality such as sugar level, root size, root color or texture, root firmness, resistance to diseases and insects, adaptability for soil and climate conditions, harvest flexibility, tolerance to drought and heat, improved post-harvest shelf-life of the leaves or postharvest quality of roots, improved standing ability in the field, improved uniformity of leaves or roots, improved bolting tolerance in seed production, improved seedling vigor, and the like.

In some embodiments, particularly desirable traits that may be incorporated by this disclosure are improved resistance to different bacterial fungal, and viral pathogens. Important diseases include but are not limited to (i) bacterial diseases such as Bacterial blight (*Pseudomonas syringae* pv. *Aptata*), Bacterial pocket (*Xanthomonas beticola*), Bacterial soft rot (*Envinia carotovora* subsp. *Carotovora*), Bacterial vascular necrosis and rot (*Envinia carotovora* subsp. *Betavasculorum*), Crown gall (*Agrobacterium tumefaciens*), Silvering disease (*Curtobacterium flaccumfaciens* pv. *betae*=*Corynebacterium betae*); (ii) fungal disease such as Alternaria leaf spot (*Alternaria alternata; Alternaria brassicae*), Anthracnose (*Colletotrichum dematium*), *Aphanomyces* root rot (black root; *Aphanomyces cochlioides*), Black wood vessel (*Pythium irregulare*), Cercospora leaf spot (*Cercospora beticola*), Charcoal rot (*Macrophomina phaseolina*), Choanephora rot (*Choanephora cucurbitarum*), Damping-off, black leg, black root and seedling blight (*Aphanomyces cochlioides; Cylindrocladium* spp. *Fusarium* spp.; *Phoma betae Pleospora; betae; Pythium* spp.; *Rhizoctonia solani; Thanatephorus cucumeris*), Downy mildew (*Peronospora farinosa; Peronospora schachtii*), Fusarium yellows (*Fusarium oxysporum*), Fusarium yellows and root rot (*Fusarium oxysporum f.sp. betae*), Leaf gall (beet tumor, or crown wart; *Physoderma leproides*), Phoma leaf spot and root rot (*Phoma betae*), Phymatotrichum root rot (cotton root rot; *Phymatotrichopsis omnivora*), Phytophthora wet rot (*Phytophthora drechsleri*), Powdery mildew (*Erysiphe polygoni*), Pythium root rot (*Pythium aphanidermatum; Pythium deliense*), Ramularia leaf spot (*Ramularia beticola*), Rhizoctonia foliar blight, crown and root rot (*Rhizoctonia solani*), Rhizopus root rot (*Rhizopus arrhizus; Rhizopus stolonifer*), Rust (*Uromyces betae*), Sclerotinia crown & root rot (*Sclerotinia sclerotiorum*), Seedling rust (*Puccinia subnitens*), Slime molds (*Physarum cinereum*), Southern blight (Sclerotium root rot and stem rot; *Sclerotium rolfsii; Athelia rolfsii*), Stemphylium leaf spot (*Stemphylium botryosum; Pleospora tarda*), Storage rots (*Botrytis cinerea: Botryotinia fuckeliana; Penicillium* spp.: *Phoma betae*), Verticillium wilt (*Verticillium albo-atrum*), Violet root rot (*Helicobasidium brebissonii; Rhizoctonia crocorum*); (iii) viral diseases such as Alfalfa mosaic virus (AMV), Beet curly top virus (BCTV), Beet distortion mosaic virus, Beet leaf curl virus (BCLV), Beet western yellows virus (BMY), Beet mosaic virus (BtMV), Beet yellow net virus (BYNV), Beet yellows virus (BYV), Cucumber mosaic virus (CMV), Lettuce infectious yellows virus (LIYV), and Beet necrotic yellow vein virus (BNYVV).

Improved resistance to insect pests is another desirable trait that may be incorporated into new beet plants developed by this disclosure. Insect pests affecting the various species of beet include Sugar beet root aphids (*Pemphigus populivenae betae*), Beet leaf miner (*Pegomya hyoscyami*), Beet webworms (*Loxostege sticticalis*), Blister beetles (*Pyrota lineata*), European Corn Borers, Flea beetles (*Psylliodes punctulata melsheimer*), Sugar beet maggots (*Tetanops myopaeformis*) and vegetable weevils.

In some embodiments, a plant of the present disclosure can be crossed with a *Beta* genus plant that is crossable (e.g., sexually compatible). The genus *Beta*, to which *B. vulgaris* belongs, is comprised of 15 recognized species which are divided into four sections: *Beta, Corollinae, Procumbentes* and *Nanae*. First, hybridization between *B. vulgaris* and specific members within the *Beta* section (i.e. fodder beet, red beet, leaf beet, Swiss chard) can occur. Successful hybridization events between *B. vulgaris* and relatives of Western European origin; *B. maritima, B. macrocarpa* and *B. atriphcifoha* (BRIDGE, 1993). Hybrids of *B. vulgaris* and *B. maritima* are fertile and show compatibility at the chromosomal level (Forster et al., 1997). Hybrids between *B. macrocarpa* and *B. vulgaris* have caused weed problems in European sugar beet fields (McFarlane, 1975). Second, artificial hybrids have been produced with species in the section Corollinae. However, such hybrids are highly sterile and few plants set seed when backcrossed to sugar beet. Third, artificial hybrids between sugar beet and members of the genus *Procumbentes* have been produced with great difficulty. The hybrids become necrotic and die at the seedling stage. The chromosomes of the species of section Procumbentes do not pair with those of the genus *Beta* (Van Geyt et al., 1990). In some embodiments, the present disclosure teaches an interspecific cross of a beet AMARENA with another species in the genus *Beta* and/or an intergeneric cross of a beet AMARENA with another species not in the genus *Beta*, but in the same family Amaranthaceae.

Beet Breeding

The goal of beet breeding is to develop new, unique and superior beet cultivar and hybrids. The breeder initially selects and crosses two or more parental lines, followed by repeated selfing and selection, producing many new genetic combinations. Another method used to develop new, unique and superior beet cultivars occurs when the breeder selects and crosses two or more parental lines followed by haploid induction and chromosome doubling that result in the development of dihaploid cultivars. The breeder can theoretically generate billions of different genetic combinations via crossing, selfing and mutations and the same is true for the utilization of the dihaploid breeding method.

Each year, the plant breeder selects the germplasm to advance to the next generation. This germplasm is grown under unique and different geographical, climatic and soil conditions, and further selections are then made, during and at the end of the growing season. The beet cultivars developed are unpredictable. This unpredictability is because the breeder's selection occurs in unique environments, with no control at the DNA level (using conventional breeding procedures or dihaploid breeding procedures), and with millions of different possible genetic combinations being generated. A breeder of ordinary skill in the art cannot predict the final resulting cultivars he develops, except possibly in a very gross and general fashion. This unpredictability results in the expenditure of large research monies to develop superior new beet cultivars.

The development of commercial beet cultivar requires the development and selection of beet plants, the crossing of these plants, and the evaluation of the crosses.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes or through the dihaploid breeding method followed by the selection of desired phenotypes. The new cultivars are evaluated to determine which have commercial potential.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

i. Pedigree Selection

Pedigree breeding is used commonly for the improvement of self-pollinating crops or inbred lines of cross-pollinating crops. Two parents possessing favorable, complementary traits are crossed to produce an $F_1$. An $F_2$ population is produced by selfing one or several $F_1$s or by intercrossing two $F_1$s (sib mating). The dihaploid breeding method could also be used. Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release of new cultivars. Similarly, the development of new cultivars through the dihaploid system requires the selection of the cultivars followed by two to five years of testing in replicated plots.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In a multiple-seed procedure, breeders commonly harvest one or more fruit containing seed from each plant in a population and blend them together to form a bulk seed lot. Part of the bulked seed is used to plant the next generation and part is put in reserve. The procedure has been referred to as modified single-seed descent or the bulk technique.

The multiple-seed procedure has been used to save labor at harvest. It is considerably faster than removing one seed from each fruit by hand for the single seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

ii. Backcross Breeding

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype recurrent parent and the trait of interest from the donor parent are selected and repeatedly crossed (backcrossed) to the recurrent parent. The resulting plant is expected to have the attributes of the recurrent parent (e.g., cultivar) and the desirable trait transferred from the donor parent.

When the term beet cultivar is used in the context of the present disclosure, this also includes any beet plant where one or more desired trait has been introduced through backcrossing methods, whether such trait is a naturally occurring one, a mutant, a transgenic one or a gene or a nucleotide sequence modified by the use of New Breeding Techniques. Backcrossing methods can be used with the present disclosure to improve or introduce one or more characteristic into the beet plant of the present disclosure. The term "backcrossing" as used herein refers to the repeated crossing of a hybrid progeny back to the recurrent parent, i.e., backcrossing one, two, three, four, five, six, seven, eight, nine, or more times to the recurrent parent. The parental beet plant which contributes the gene or the genes for the desired characteristic is termed the nonrecurrent or donor parent. This terminology refers to the fact that the nonrecurrent parent is used one time in the backcross protocol and therefore does not recur. The parental beet cultivar to which the gene or genes from the nonrecurrent parent are transferred is known as the recurrent parent as it is used for several rounds in the backcrossing protocol.

In a typical backcross protocol, the original cultivar of interest (recurrent parent) is crossed to a second cultivar (nonrecurrent parent) that carries the gene or genes of interest to be transferred. The resulting progeny from this cross are then crossed again to the recurrent parent and the process is repeated until a beet plant is obtained wherein all of the desired morphological and physiological characteristics of the recurrent parent are recovered in the converted plant, generally determined at a 5% significance level when grown in the same environmental conditions, in addition to the gene or genes transferred from the nonrecurrent parent. It has to be noted that some, one, two, three or more, self-pollination and growing of population might be included between two successive backcrosses. Indeed, an appropriate selection in the population produced by the self-pollination, i.e. selection for the desired trait and physiological and morphological characteristics of the recurrent parent might be equivalent to one, two or even three additional backcrosses in a continuous series without rigorous selection, saving then time, money and effort to the breeder. A non-limiting example of such a protocol would be the following: a) the first generation F1 produced by the cross of the recurrent parent A by the donor parent B is backcrossed to parent A, b) selection is practiced for the plants having the desired trait of parent B, c) selected plant are self-pollinated to produce a population of plants where selection is practiced for the plants having the desired trait of parent B and physiological and morphological characteristics of parent A, d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute one or more trait(s) or characteristic(s) in the original inbred parental line in order to find it then in the hybrid made thereof. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important that the identification of the character(s) in the segregating population. In this instance it may then be necessary to introduce a test of the progeny to determine if the desired characteristic(s) has been successfully transferred. Such tests encompass visual inspection, simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the waxy starch characteristic in corn, require selfing the progeny to determine which plant carry the recessive allele(s).

Many single gene traits have been identified that are not regularly selected for in the development of a beet plant according to the disclosure but that can be improved by backcrossing techniques. Single gene traits may or may not be transgenic. Examples of these traits include but are not limited to, herbicide resistance, resistance or tolerance to an bacterial, fungal or viral infection as well as insect pests. Many single gene traits have been identified that are not regularly selected for in the development of a new line but that can be improved by backcrossing techniques. Single gene traits may or may not be transgenic. Traits for resistance or tolerance to an infection by a virus, a bacterium, an insect or a fungus may also be introduced. Such traits may come from another beet plant, or a different plant species.

These genes are generally inherited through the nucleus. Some other single gene traits, for example, in corns are described in U.S. Pat. Nos. 5,777,196, 5,948,957, and 5,969,212, the disclosures of which are specifically hereby incorporated by reference.

Also, desired genes and/or traits can be introduced and/or transferred among beet plants, which are well described in Bilgen T at al. (1969, J Am Soc Sugar Beet Technol 15:444-449); Lange W et al. (1990, Proceedings 53rd Winter Congress, International Institute for Sugar Beet Research, pp. 89-102); Sandal, N. N. et al. (1997, Molecular Breeding 3, 471-480); Lewellen, R. T. et al. (2001, Plant Disease, 85(6):627-631); Mackay, I J et al. (1999, Theoretical and Applied Genetics; Heidelberg Vol. 98, Iss. 6-7,: 1156-1162); U.S. Pat. No. 9,198,364; International Application Pulication No. WO2020053313, all the disclosures of which are specifically hereby incorporated by reference.

In 1981, the backcross method of breeding counted for 17% of the total breeding effort for inbred line development in the United States, accordingly to, Hallauer, A. R. et al. (1988) "Corn Breeding" Corn and Corn Improvement, No. 18, pp. 463-481.

The backcross breeding method provides a precise way of improving varieties that excel in a large number of attributes but are deficient in a few characteristics. (Page 150 of the Pr. R. W. Allard's 1960 book, published by John Wiley & Sons, Inc, *Principles of Plant Breeding*). The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a parental line of a hybrid variety with exactly or essentially the same adaptation, yielding ability and quality characteristics of the recurrent parent but superior to that parent in the particular characteristic(s) for which the improvement program was undertaken. Therefore, this method provides the plant breeder with a high degree of genetic control of this work.

The method is scientifically exact because the morphological and agricultural features of the improved variety could be described in advance and because a similar variety could, if it were desired, be bred a second time by retracing the same steps (Briggs, "Breeding wheats resistant to bunt by the backcross method", 1930 *Jour. Amer. Soc. Agron.*, 22: 289-244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be theoretically modified only with regards to genes being transferred, which are maintained in the population by selection.

Successful backcrosses are, for example, the transfer of stem rust resistance from 'Hope' wheat to 'Bart wheat' and even pursuing the backcrosses with the transfer of bunt resistance to create 'Bart 38', having both resistances. Also highlighted by Allard is the successful transfer of mildew, leaf spot and wilt resistances in California Common alfalfa to create 'Caliverde'. This new 'Caliverde' variety produced through the backcross process is indistinguishable from California Common except for its resistance to the three named diseases.

One of the advantages of the backcross method is that the breeding program can be carried out in almost every environment that will allow the development of the character being transferred or when using molecular markers that can identify the trait of interest.

The backcross technique is not only desirable when breeding for disease resistance but also for the adjustment of morphological characters, color characteristics and simply inherited quantitative characters such as earliness, plant height and seed size and shape. In this regard, a medium grain type variety, 'Calady', has been produced by Jones and Davis. As dealing with quantitative characteristics, they selected the donor parent with the view of sacrificing some of the intensity of the character for which it was chosen, i.e. grain size. 'Lady Wright', a long grain variety was used as the donor parent and 'Coloro', a short grain one as the recurrent parent. After four backcrosses, the medium grain type variety 'Calady' was produced.

iii. Open-Pollinated Populations

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity.

Uniformity in such populations is impossible and trueness-to-type in an open-pollinated variety is a statistical feature of the population as a whole, not a characteristic of individual plants.

Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement.

First, there is the situation in which a population is changed en masse by a chosen selection procedure. The outcome is an improved population that is indefinitely propagated by random-mating within itself in isolation.

Second, the synthetic variety attains the same end result as population improvement, but is not itself propagated as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

A) Mass Selection

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

B) Synthetics

A synthetic variety is produced by intercrossing a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or more cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

iv. Hybrids

A hybrid is an individual plant resulting from a cross between parents of differing genotypes. Commercial hybrids are now used extensively in many crops, including corn (maize), sorghum, sugarbeet, beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an outbreeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

Once the inbreds/cultivars that give the best hybrid performance have been identified, the hybrid seed can be reproduced indefinitely as long as the homogeneity of the inbred parent is maintained. A single-cross hybrid is produced when two inbred lines are crossed to produce the F1 progeny. A double-cross hybrid is produced from four inbred lines crossed in pairs (A×B and C×D) and then the two F1 hybrids are crossed again (A×B)×(C×D). Much of the hybrid vigor and uniformity exhibited by F1 hybrids is lost in the next generation (F2). Consequently, seed from F2 hybrid varieties is not used for planting stock.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

v. Bulk Segregation Analysis (BSA)

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA*, 99:9828-9832) and Quarrie et al. (Quarrie et al., 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs, SNPs or SSRs). Markers linked to the phenotype can be identified and used for breeding or QTL mapping.

vi. Hand-Pollination Method

Hand pollination describes the crossing of plants via the deliberate fertilization of female ovules with pollen from a desired male parent plant. In some embodiments the donor or recipient female parent and the donor or recipient male parent line are planted in the same field. In some embodiments the donor or recipient female parent and the donor or recipient male parent line are planted in the same greenhouse. The inbred male parent can be planted earlier than the female parent to ensure adequate pollen supply at the pollination time. In some embodiments, the male parent and female parent can be planted at a ratio of 1 male parent to 4-10 female parents. The male parent may be planted at the top of the field for efficient male flower collection during pollination. Pollination is started when the female parent flower is ready to be fertilized. Female flower buds that are ready to open in the following days are identified, covered with paper cups or small paper bags that prevent bee or any other insect from visiting the female flowers, and marked with any kind of material that can be easily seen the next morning. In some embodiments, this process is best done in the afternoon. The male flowers of the male parent are collected in the early morning before they are open and visited by pollinating insects. The covered female flowers of the female parent, which have opened, are un-covered and pollinated with the collected fresh male flowers of the male parent, starting as soon as the male flower sheds pollen. The pollinated female flowers are again covered after pollination to prevent bees and any other insects visit. The pollinated female flowers are also marked. The marked flowers are harvested. In some embodiments, the male pollen used for fertilization has been previously collected and stored.

vii. Bee-Pollination Method

Using the bee-pollination method, the parent plants are usually planted within close proximity. In some embodiments more female plants are planted to allow for a greater production of seed. Insects are placed in the field or greenhouses for transfer of pollen from the male parent to the female flowers of the female parent.

viii. Targeting Induced Local Lesions in Genomes (TILLING)

Breeding schemes of the present application can include crosses with TILLING® plant cultivars. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and beet.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. As DNA bases are not pairing at the mismatch of the two DNA strands (the induced mutation in TILLING® or the natural mutation or SNP in EcoTILLING), they provoke a shape change in the double strand DNA fragment which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus;* John Innes Centre (UK), focusing on *Brassica rapa;* Fred Hutchinson Cancer Research, focusing on Arabidopsis; Southern Illinois University (USA), focusing on Soybean; John Innes Centre (UK), focusing on Lotus and Medicago; and INRA (France), focusing on Pea and Tomato.

More detailed description on methods and compositions on TILLING® can be found in U.S. Pat No. 599,4075, U.S. 2004/0053236 A1, WO 2005/055704, and WO 2005/048692, each of which is hereby incorporated by reference for all purposes.

Thus in some embodiments, the breeding methods of the present disclosure include breeding with one or more TILLING plant lines with one or more identified mutations.

ix. Mutation Breeding

Mutation breeding is another method of introducing new variation and subsequent traits into beet plants. Mutations that occur spontaneously or are artificially induced can be useful sources of variability for a plant breeder. The goal of artificial mutagenesis is to increase the rate of mutation for a desired characteristic. Mutation rates can be increased by many different means or mutating agents including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in W. R. Fehr, 1993, Principles of Cultivar Development, Macmillan Publishing Co.

New breeding techniques such as the ones involving the uses of Zinc Finger Nucleases or oligonucleotide directed mutagenesis may also be used to generate genetic variability and introduce new traits into beet varieties.

x. Double Haploids and Chromosome Doubling

One way to obtain homozygous plants without the need to cross two parental lines followed by a long selection of the segregating progeny, and/or multiple backcrossing is to produce haploids and then double the chromosomes to form doubled haploids. Haploid plants can occur spontaneously, or may be artificially induced via chemical treatments or by crossing plants with inducer lines (Seymour et al. 2012, PNAS vol 109, pg 4227-4232; Zhang et al., 2008 Plant Cell Rep. Dec. 27(12) 1851-60). The production of haploid progeny can occur via a variety of mechanisms which can affect the distribution of chromosomes during gamete formation. The chromosome complements of haploids sometimes double spontaneously to produce homozygous doubled haploids (DHs). Mixoploids, which are plants which contain cells having different ploidies, can sometimes arise and may represent plants that are undergoing chromosome doubling so as to spontaneously produce doubled haploid tissues, organs, shoots, floral parts or plants. Another common technique is to induce the formation of double haploid plants with a chromosome doubling treatment such as colchicine (El-Hennawy et al., 2011 Vol 56, issue 2 pages 63-72; Doubled Haploid Production in Crop Plants 2003 edited by Maluszynski ISBN 1-4020-1544-5). The production of doubled haploid plants yields highly uniform cultivars and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar development.

xi. Protoplast Fusion

In another method for breeding plants, protoplast fusion can also be used for the transfer of trait-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell may even be obtained with plant species that cannot be interbred in nature is tissue cultured into a hybrid plant exhibiting the desirable combination of traits.

xii. Embryo Rescue

Alternatively, embryo rescue may be employed in the transfer of resistance-conferring genomic material from a donor plant to a recipient plant. Embryo rescue can be used as a procedure to isolate embryos from crosses to rapidly move to the next generation of backcrossing or selfing or wherein plants fail to produce viable seed. In this process, the fertilized ovary or immature seed of a plant is tissue cultured to create new plants (see Pierik, 1999, *In Vitro Culture of Higher Plants*, Springer, ISBN 079235267, 9780792352679, which is incorporated herein by reference in its entirety).

Breeding Evaluation

Each breeding program can include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s). The best lines are candidates for use as parents in new commercial cultivars; those still deficient in a few traits may be used as parents to produce new populations for further selection or in a backcross program to improve the parent lines for a specific trait.

In one embodiment, the plants are selected on the basis of one or more phenotypic traits. Skilled persons will readily appreciate that such traits include any observable characteristic of the plant, including for example growth rate, vigor, plant health, maturity, branching, plant height, leaf coverage, weight, total yield, color, taste, sugar levels, aroma, changes in the production of one or more compounds by the plant (including for example, metabolites, proteins, drugs, carbohydrates, oils, and any other compounds).

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Selecting plants based on genotypic information is also envisaged (for example, including the pattern of plant gene expression, genotype, or presence of genetic markers). Where the presence of one or more genetic marker is assessed, the one or more marker may already be known and/or associated with a particular characteristic of a plant; for example, a marker or markers may be associated with an increased growth rate or metabolite profile. This information could be used in combination with assessment based on other characteristics in a method of the disclosure to select for a combination of different plant characteristics that may be desirable. Such techniques may be used to identify novel quantitative trait loci (QTLs). By way of example, plants may be selected based on growth rate, size (including but not limited to weight, height, leaf size, stem size, branching pattern, or the size of any part of the plant), general health, survival, tolerance to adverse physical environments and/or any other characteristic, as described herein before.

Further non-limiting examples include selecting plants based on: speed of seed germination; quantity of biomass produced; increased root, and/or leaf/shoot growth that leads to an increased yield (herbage or grain or fiber or oil) or biomass production; effects on plant growth that results in an increased root and/or seed yield for a crop; effects on plant growth which result in an increased head yield; effects on plant growth that lead to an increased resistance or tolerance to disease including fungal, viral or bacterial diseases, to mycoplasma, or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields; effects on plant growth that lead to improved aesthetic appeal which may be particularly important in plants grown for their form, color or taste, for example the color intensity of beet leaves/roots, or the taste of said leaves/roots.

Molecular Breeding Evaluation Techniques

Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (Transcriptome Sequencing), qRTPCR (quantitative real time PCR).

In one embodiment, the evaluating step of a plant breeding program involves the identification of desirable traits in progeny plants. Progeny plants can be grown in, or exposed to conditions designed to emphasize a particular trait (e.g. drought conditions for drought tolerance, lower temperatures for freezing tolerant traits). Progeny plants with the highest scores for a particular trait may be used for subsequent breeding steps.

In some embodiments, plants selected from the evaluation step can exhibit a 1%, 5%, 10%, 15%, 20%, 25%, 30%, 35%, 40%, 45%, 50%, 55%, 60%, 65%, 70%, 75%, 80%, 85%, 90%, 95%, 100%, 120% or more improvement in a particular plant trait compared to a control plant.

In other embodiments, the evaluating step of plant breeding comprises one or more molecular biological tests for genes or other markers. For example, the molecular biological test can involve probe hybridization and/or amplification of nucleic acid (e.g., measuring nucleic acid density by Northern or Southern hybridization, PCR) and/or immunological detection (e.g., measuring protein density, such as precipitation and agglutination tests, ELISA (e.g., Lateral Flow test or DAS-ELISA), Western blot, immune labeling, immunosorbent electron microscopy (ISEM), and/or dot blot).

The procedure to perform a nucleic acid hybridization, an amplification of nucleic acid (e.g., PCR, RT-PCR) or an immunological detection (e.g., precipitation and agglutination tests, ELISA (e.g., Lateral Flow test or DAS-ELISA), Western blot, RIA, immunogold or immunofluorescent labeling, immunosorbent electron microscopy (ISEM), and/or dot blot tests) are performed as described elsewhere herein and well-known by one skilled in the art.

In one embodiment, the evaluating step comprises PCR (semi-quantitative or quantitative), wherein primers are used to amplify one or more nucleic acid sequences of a desirable gene, or a nucleic acid associated with said gene, or QTL or a desirable trait (e.g., a cosegregating nucleic acid, or other marker).

In another embodiment, the evaluating step comprises immunological detection (e.g., precipitation and agglutination tests, ELISA (e.g., Lateral Flow test or DAS-ELISA), Western blot, RIA, immuno labeling (gold, fluorescent, or other detectable marker), immunosorbent electron microscopy (ISEM), and/or dot blot), wherein one or more gene or marker-specific antibodies are used to detect one or more desirable proteins. In one embodiment, said specific antibody is selected from the group consisting of polyclonal antibodies, monoclonal antibodies, antibody fragments, and combination thereof.

Reverse Transcription Polymerase Chain Reaction (RT-PCR) can be utilized in the present disclosure to determine expression of a gene to assist during the selection step of a breeding scheme. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR.

RT-PCR utilizes a pair of primers, which are complementary to a defined sequence on each of the two strands of the mRNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 60° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cation concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using for example agarose gel electrophoresis or other polymer gel-like polyacrylamide gels and ethidium bromide (or other nucleic acid staining).

Conventional RT-PCR is a time-consuming technique with important limitations when compared to real time PCR techniques. This, combined with the fact that ethidium bromide has low sensitivity, yields results that are not always reliable. Moreover, there is an increased cross-contamination risk of the samples since detection of the PCR product requires the post-amplification processing of the samples. Furthermore, the specificity of the assay is mainly determined by the primers, which can give false-positive results. However, the most important issue concerning conventional RT-PCR is the fact that it is a semi- or even a low-quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general non-specific DNA Binding Dyes such as SYBR Green I, TaqMan Probes and Molecular Beacons (including Scorpions).

The real-time PCR thermal cycler has a fluorescence detection threshold, below which it cannot discriminate the difference between amplification-generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification-generated fluorescence from the background noise is called the threshold cycle (Ct). The higher is the initial DNA concentration, the lower its Ct will be.

Other forms of nucleic acid detection can include next-generation sequencing methods such as DNA SEQ or RNA SEQ using any known sequencing platform including, but not limited to: Roche 454, Solexa Genome Analyzer, AB SOLiD, Illumina GA/HiSeq, Ion PGM, Mi Seq, among others (Liu et al,. 2012 Journal of Biomedicine and Biotechnology Volume 2012 ID 251364; Franca et al., 2002 Quarterly Reviews of Biophysics 35 pg 169-200; Mardis 2008 Genomics and Human Genetics vol 9 pg 387-402).

In other embodiments, nucleic acids may be detected with other high-throughput hybridization technologies including microarrays, gene chips, LNA probes, nanoStrings, and fluorescence polarization detection, among others.

In some embodiments, detection of markers can be achieved at an early stage of plant growth by harvesting a small tissue sample (e.g., branch, or leaf disk). This approach is preferable when working with large populations as it allows breeders to weed out undesirable progeny at an early stage and conserve growth space and resources for progeny which show more promise. In some embodiments the detection of markers is automated, such that the detection and storage of marker data is handled by a machine. Recent advances in robotics have also led to full service analysis tools capable of handling nucleic acid/protein marker extractions, detection, storage and analysis.

Quantitative Trait Loci

Breeding schemes of the present application can include crosses between donor and recipient plants. In some embodiments said donor plants contain a gene or genes of interest which may confer the plant with a desirable phenotype. The recipient line can be an elite line or cultivar having certain favorable traits for commercial production. In one embodiment, the elite line may contain other genes that also impart said line with the desired phenotype. When crossed together, the donor and recipient plant may create a progeny plant with combined desirable loci which may provide quantitatively additive effect of a particular characteristic. In that case, QTL mapping can be involved to facilitate the breeding process.

A QTL (quantitative trait locus) mapping can be applied to determine the parts of the donor plant's genome conferring the desirable phenotype, and facilitate the breeding methods. Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. yield, height, level of resistance to virus, etc.) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait. Knowing the number of QTLs that explains variation in the phenotypic trait tells about the genetic architecture of a trait. It may tell that a trait is controlled by many genes of small effect, or by a few genes of large effect or by a several genes of small effect and few genes of larger effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping*, 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing one or several genes, i.e. a cluster of genes that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and how those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, SNPs, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes are generally 50%. Between molecular markers located on the same chromosome the recombination frequency depends on the distance between the markers. A low recombination frequency usually corresponds to a low distance between markers on a chromosome. Comparing all recombination frequencies will result in the most logical order of the molecular markers on the chromosomes. This most logical order can be depicted in a linkage map (Paterson, 1996, Genome Mapping in Plants. R. G. Landes, Austin.). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with a desirable trait in a donor plant can be transferred to a recipient plant to incorporate the desirable trait into progeny plants by transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near-isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred to as near-isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL usually cover the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTLs affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, *PLoS Biol.*; 2(10):e245).

Tissue Culture

As it is well known in the art, tissue culture of beet can be used for the in vitro regeneration of beet plants. Tissues cultures of various tissues of beet and regeneration of plants therefrom are well known and published. For example, reference may be had to S. Mezei, L. Kovacev & N. Nagl (2006) Sugar Beet Micropropagation, Biotechnology & Biotechnological Equipment, 20:1, 9-14; G. HUSSEY, A. HEPHER (1978) Clonal Propagation of Sugar Beet Plants and the Formation of Polyploids by Tissue Culture, Annals of Botany, Volume 42, Issue 2, March 1978, Pages 477-479; Xu, Q. L., Xie, Y. H., Ru, H. et al. Efficient plant regeneration in vitro from red leaf beet via organogenesis. Russ J Plant Physiol 56, 546-550 (2009); Polishchuk, V. V., Karpuk, L. M., Mykolaiko, V. P., Polishchuk, A. A., & Mykolaiko, I. I. (2017). In vitro rhizogenesis of sugar beet microclones. Regulatory Mechanisms in Biosystems, 8(4), 616-622, the disclosures of which are incorporated herein by reference.

It is clear from the literature that the state of the art is such that these methods of obtaining plants are routinely used and have a high rate of success. Thus, another aspect of this disclosure is to provide cells which upon growth and differentiation produce beet plants having all of the physiological and morphological characteristics of beet cultivar AMARENA.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, crowns, roots, rootlets, taproots, root tips, anthers, pistils, meristematic cells, axillary buds, ovaries, seed coat, endosperm, hypocotyls, cotyledons and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

EXAMPLES

The foregoing examples of the related art and limitations related therewith are intended to be illustrative and not exclusive. Other limitations of the related art will become apparent to those of skill in the art upon a reading of the specification.

Example 1—Development of beet cultivar AMARENA

Beet cultivar AMARENA is a beet to be used in beet root production, with an adequate root size, length, volume, color and texture. It is a beet variety with mainly red leaves including very strong red color in its veins and very weak green color in its blades. The leaves tend to curl and their front is shiny. AMARENA has medium-elliptic leaves with medium undulate margin and weak leaf blistering. BB218 midrib curvature is medium v-shaped. Leaf tends to curl. Its roots has an obovate shape in its longitudinal section with a pointed root tip, while its root corkiness is weak. The external surface and main flesh of AMARENA roots are purple. The bolting from an early sowing is weak.

Breeding History:

Beet cultivar AMARENA was an outcome of a cross between RUBENS, a proprietary red beet variety wholly owned by Vilmorin-Mikado S. A. and BB 16001, a proprietary red beet breeding line with superior leaf characteristics, followed by a series of selections and subsequence selfings. The AMARENA breeding was made at the Vilmorin-Mikado research facilities in Odense, Syddanmark, D K. The red beet variety RUBENS is registered with grant/registration number 36877 for Plant Breeder's Rights (PBR) in Europe.

A series of individual plant selections and subsequent selfings started in the second year of development in Odense, DK where unique individuals were selected in the F1 generation after the cross between RUBENS and BB 16001 and were allowed to self-pollinate. From the F1 generation, a pedigree selection method was maintained from the F2 generation to the F5 generation where self-pollination was deployed and selection was done based on the criteria of increased seedling vigor, consistency in the red leaf color, root shape uniformity, and resistance towards *Pseudomonas syringae* var. *aptata*. The line was deemed stable at the F5 generation. In the F5 generation, selected plants were grown in an isolated area and allowed to intermate via open-pollination. Seeds of the F6 generation were then bulked, and this seed was then used as breeder stock seeds towards advancement of the variety.

This method of sowing, selfing and selecting was done over several years until the desired phenotypic uniformity was achieved in the F6 generation, and this seed lot had the number designation AMARENA.

Some of the agronomical criteria used to select the beet cultivar AMARENA in various generations include increased seedling vigor, consistency in leaf color, root uniformity, and resistance towards *Pseudomonas syringae* var. *aptata*.

The beet cultivar AMARENA has shown uniformity and stability for the traits, within the limits of environmental influence for the traits as described in the following Variety Descriptive Information. No variant traits have been observed or are expected for agronomical important traits in the beet cultivar AMARENA.

Beet cultivar AMARENA has the following morphologic and other characteristics, (based primarily on data collected at the Vimorin-Mikado research facilities in Gilroy, Calif., all experiments done under the direct supervision of the applicant). AMARENA was compared to a check variety 'RUBENS', and showed distinct phenotypes as presented in Table 1.

TABLE 1

Variety Description Information

| Characteristic | AMARENA | RUBENS |
|---|---|---|
| 1. Germity | Multigerm | multigerm |
| 2. Seedling: red coloration of hypocotyl | Present, 8 | Present, 7 |
| 3. Leaf; Attitude of petiole | Erect, 2 | Semi erect, 4 |
| 4. Leaf: attitude of blade | Semi-erect, 3 | Semi-erect, 4 |
| 5. Leaf: length (including petiole) | Medium long, 7 | Medium, 6 |
| 6. Leaf Blade: length | Medium long, 6 | Medium, 5 |
| 7. Leaf Blade: Width | Medium, 5 | Medium broad, 6 |
| 8. Leaf Blade: Shape | Medium elliptic, 6 | Broad elliptic, 7 |
| 9. Leaf Blade: color | Mainly red, 6 | Mainly red, 4 |
| 10. Leaf Blade: intensity of green color | Very Weak, 1 | Very weak, 2 |
| 11. Leaf Blade: red coloration of veins | Very strong, 9 | Very Strong, 8 |
| 12. Leaf Blade: undulation of margin | Medium, 6 | Strong, 7 |
| 13. Leaf Blade: blistering | Weak, 3 | Weak, 3 |
| 14. Petiole width of base (at root insertion) | Narrow, 3 | Narrow, 4 |
| 15. Petiole main color of lower side | Purple, 6 | Purple, 6 |
| 16. Root position in soil | Medium shallow, 4 | Medium deep, 6 |
| 17. Root shape in longitudinal section | Obovate, 4 | Circular, 3 |
| 18. Root Length | Medium, 5 | Medium short, 4 |
| 19. Root width | Medium, 5 | Broad, 7 |
| 20. Root length/width ratio | Medium, 3 | Medium small, 2 |
| 21. Root shape of tip | Pointed, 1 | Rounded, 2 |
| 22. Root corkiness | Weak, 2 | Weak, 2 |
| 23. Root external color | Purple, 4 | Reddish purple, 3 |
| 24. Root main color of flesh | Purple, 5 | Purple, 4 |
| 25. Root intensity of main color of flesh | Dark, 7 | Dark, 6 |
| 26. Root prominence of rings | Medium, 5 | Medium, 6 |
| 27. Bolting tendency (from an early sowing) | Weak, 1 | Medium weak, 3 |

DEPOSIT INFORMATION

A deposit of the beet seed of this disclosure is maintained by Vilmorin-Mikado S. A., Route du Manoir, 49250 La Ménitré, France. In addition, a sample of the beet seed of this disclosure has been deposited with the National Collections of Industrial, Food and Marine Bacteria (NCIMB), NCIMB Ltd. Ferguson Building, Craibstone Estate, Bucksburn, Aberdeen, AB21 9YA Scotland. The deposit for beet cultivar AMARENA was made on Apr. 12, 2021.

To satisfy the enablement requirements of 35 U.S.C. 112, and to certify that the deposit of the isolated strain of the present disclosure meets the criteria set forth in 37 C.F.R. 1.801-1.809, Applicants hereby make the following statements regarding the deposited beet cultivar AMARENA (deposited as NCIMB Accession No. 43761):

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 C.F.R. 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the NCIMB.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

OTHER REFERENCES

BRIDGE (Biotechnology Research for Innovation, Development and Growth in Europe) 1993. Safety Assessment of the Deliberate Release of Two Model Transgenic Plants. Oilseed Rape and Sugar Beet. European Community funded BRIDGE project BIOT CT-910298.

Forster, V., Marrese, D., Staska, K., Trinks, K., and J. R. Stander. 1997. Petition for Determination of Nonregulated Status: Glufosinate Tolerant Sugar Beet, Transformation Event T120-7. AgrEvo USA Comapany, Wilmington, Del.. 67 pp.

McFarlane, J. S. 1975. Naturally Occurring Hybrids Between Sugar Beet and *Beta macrocarpa* in the Imperial Valley of California. Journal of the A.S.S.B.T. 18:245-251.

Van Geyt, J. P. C., Lange, W., Oleo, M. & Th. S. M. De Bock, 1990. Natural variation within the genus *Beta* and its possible use for breeding sugar beet: A review. Euphytica 49:57-76.

Bilgen T, Gaskill J O, Hecker R J, Wood D R (1969) Transferring Cercospora leaf spot resistance from *Beta maritima* to sugarbeet by backcrossing. J Am Soc Sugar Beet Technol 15:444-449

Lange W, Jung C, Heijbroek W: Transfer of beet cyst nematode resistance from *Beta* species of the section Patellares to cultivated beet. Proceedings 53rd Winter Congress, International Institute for Sugar Beet Research, pp. 89-102 (1990).

Sandal, N. N., Salentijn, E. M., Kleine, M. et al. Backcrossing of nematode-resistant sugar beet: a second nematode resistance gene at the locus containing Hs1pro-1?. Molecular Breeding 3, 471-480 (1997).

Lewellen, R. T. and Schrandt, J. K. Inheritance of Powdery Mildew Resistance in Sugar Beet Derived from *Beta vulgaris* subsp. *Maritima*, Plant Disease, 85(6):627-631 (2001).

Mackay, I J; Gibson, J P; Caligari, P D S.. The genetics of selfing with concurrent backcrossing in breeding hybrid sugar beet (*Beta vulgaris altissima* L.) Theoretical and Applied Genetics; Heidelberg Vol. 98, Iss. 6-7, (May 1999): 1156-1162.

U.S. Pat. No. 919,8364

World Patent No. WO2020053313

What is claimed is:

1. A seed of beet designated AMARENA, wherein a representative sample of seed of said beet has been deposited under NCIMB No. 43761.

2. A beet plant, a plant part thereof or a plant cell thereof, produced by growing the seed of claim 1.

3. The beet plant part or a plant cell thereof of claim 2, wherein the beet part is selected from the group consisting of a crown, a leaf, a flower, a cotyledon, a hypocotyl, a stem, a shoot, a root, a rootlet, a taproot, a root tip, a fruit, a stalk, a seed, an embryo, a stamen, an anther, a pistil, a pollen, an ovule, and a cell.

4. A beet plant, a plant part, or a plant cell thereof, wherein the plant or a plant regenerated from the plant part or the plant cell has all of the physiological and morphological characteristics of beet designated AMARENA deposited under NCIMB No. 43761 when grown under the same environmental conditions.

5. A tissue culture of regenerable cells produced from the plant or the plant part or the plant cell of claim 2, wherein a plant regenerated from the tissue culture has all of the physiological and morphological characteristics of beet AMARENA deposited under NCIMB No. 43761 when grown in the same environmental conditions.

6. A beet plant regenerated from the tissue culture of claim 5, wherein said plant has all of the physiological and morphological characteristics of AMARENA deposited under NCIMB No. 43761 when grown under the same environmental conditions.

7. A beet leaf and/or root produced from the plant of claim 2.

8. A method for producing a beet leaf and/or root, the method comprising: a) growing the beet plant of claim 2 to produce a beet leaf and/or root, and b) harvesting said beet leaf and/or root.

9. A beet leaf and/or root produced by the method of claim 8.

10. A method for producing a beet seed, the method comprising: crossing a first parent beet plant with a second parent beet plant and harvesting the resultant beet seed, wherein said first parent beet plant and/or second parent beet plant is the beet plant of claim 2.

11. A beet seed produced by the method of claim 10, wherein the beet seed or a beet plant produced by growing the seed comprises all of the physiological and morphological characteristics of beet designated AMARENA.

12. A method for producing a beet seed, the method comprising: self-pollinating the beet plant of claim 2 and harvesting the resultant beet seed.

13. A beet seed produced by the method of claim 12, wherein the beet seed or a beet plant produced by growing the seed comprises all of the physiological and morphological characteristics of beet designated AMARENA.

14. A method of vegetatively propagating the beet plant of claim 2, the method comprising: (a) collecting a part capable of being propagated from the plant of claim 2 and (b) regenerating a plant from said part.

15. The method of claim 14, further comprising (c) harvesting a beet leaf and/or root from said regenerated plant.

16. A beet leaf and/or root obtained from the method of claim 15.

17. A method of producing a beet plant derived from the beet AMARENA, the method comprising:
  (a) crossing the plant of claim 2 with a second beet plant to produce a progeny plant.

18. The method of claim 17, further comprising the steps of:
  (b) crossing the progeny plant derived from beet AMARENA with itself or a second beet plant to produce a seed of a progeny plant of subsequent generation;
  (c) growing the progeny plant of the subsequent generation from the seed;
  (d) crossing the progeny plant of the subsequent generation with itself or a second beet plant to produce a beet plant derived from the beet AMARENA; and
  (e) repeating step (b) and/or (c) to produce a beet plant further derived from the beet AMARENA.

19. A method of producing a beet plant designated AMARENA comprising at least one desired trait, the method comprising: introducing a single locus conversion conferring the desired trait into the beet AMARENA, whereby a beet plant designated AMARENA comprising the desired trait is produced.

20. A beet plant, comprising: a single locus conversion and all of the characteristics of AMARENA deposited under NCIMB No. 43761 when grown under the same environmental conditions.

21. The plant of claim 20, wherein the single locus conversion confers said plant with herbicide resistance.

22. The plant of claim 20, wherein the single locus conversion is introduced into the plant by the use of recurrent selection, mutation breeding, wherein said mutation breeding selects for a mutation that is spontaneous or artificially induced, backcrossing, pedigree breeding, haploid/double haploid production, marker-assisted selection, genetic transformation, genomic selection, Zinc finger nuclease (ZFN) technology, oligonucleotide directed mutagenesis, cisgenesis, intragenesis, RNA-dependent DNA methylation, agro-infiltration, Transcription Activation-Like Effector Nuclease (TALENs), CRISPR/Cas system, engineered meganuclease, re-engineered homing endonuclease, and DNA guided genome editing.

23. A method for producing nucleic acids, the method comprising: isolating nucleic acids from the plant of claim 2, or a plant part, or a plant cell thereof.

24. A method for producing a second beet plant, the method comprising: applying a plant breeding technique to the plant or plant part of claim 2 to produce the second beet plant.

25. A method of introducing a desired trait into a beet plant designated AMARENA, the method comprising:

(a) crossing a beet AMARENA plant grown from beet AMARENA seed, wherein a representative sample of seed has been deposited under NCIMB No. 43761, with another beet plant or a *Beta* plant sexually compatible with beet that comprises a desired trait to produce F1 progeny plants;
(b) selecting one or more progeny plants that have the desired trait to produce selected progeny plants;
(c) crossing the selected progeny plants with the beet AMARENA plants to produce backcross progeny plants;
(d) selecting for backcross progeny plants that have the desired trait and essentially all of the physiological and morphological characteristics of beet AMARENA deposited under NCIMB No. 43761 when grown in the same environmental conditions to produce selected backcross progeny plants; and
(e) repeating steps (c) and (d) three or more times in succession to produce selected fourth or higher backcross progeny plants that comprise the desired trait and essentially all of the physiological and morphological characteristics of beet AMARENA deposited under NCIMB No. 43761 when grown in the same environmental conditions.

* * * * *